US012589220B2

(12) United States Patent
Burkholz et al.

(10) Patent No.: US 12,589,220 B2
(45) Date of Patent: Mar. 31, 2026

(54) INSTRUMENT DELIVERY DEVICE WITH NESTED HOUSING

(71) Applicant: Becton, Dickinson and Company, Franklin Lakes, NJ (US)

(72) Inventors: Jonathan Karl Burkholz, Salt Lake City, UT (US); Megan S. Scherich, Salt Lake City, UT (US); Curtis H. Blanchard, Herriman, UT (US); Shaun Lauer, Portland, OR (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 804 days.

(21) Appl. No.: 17/901,049

(22) Filed: Sep. 1, 2022

(65) Prior Publication Data

US 2024/0075248 A1 Mar. 7, 2024

(51) Int. Cl.
*A61M 25/01* (2006.01)
*A61M 25/00* (2006.01)

(52) U.S. Cl.
CPC .... *A61M 25/0102* (2013.01); *A61M 25/0021* (2013.01); *A61M 25/0043* (2013.01)

(58) Field of Classification Search
CPC .......... A61M 25/0102; A61M 25/0606; A61M 39/10; A61M 39/1055; A61M 25/0141; A61M 25/008; A61M 2025/0062; A61M 2039/0673; A61B 5/153
See application file for complete search history.

(56) References Cited

U.S. PATENT DOCUMENTS

| | | | | |
|---|---|---|---|---|
| 5,647,846 A | * | 7/1997 | Berg ................. | A61M 25/0023 |
| | | | | 604/93.01 |
| 6,007,478 A | * | 12/1999 | Siess ................. | A61M 25/0053 |
| | | | | 600/585 |
| 9,114,229 B2 | | 8/2015 | Fuentes | |
| 11,389,624 B2 | | 7/2022 | Cook | |
| 2009/0105692 A1 | * | 4/2009 | Lopez .................. | A61M 39/12 |
| | | | | 604/535 |

(Continued)

FOREIGN PATENT DOCUMENTS

| | | |
|---|---|---|
| WO | 2021236530 A1 | 11/2021 |
| WO | 2022032242 A1 | 2/2022 |

OTHER PUBLICATIONS

U.S. Appl. No. 63/273,226, Becton, Dickinson and Company, filed Oct. 29, 2021.

(Continued)

*Primary Examiner* — Nilay J Shah
(74) *Attorney, Agent, or Firm* — The Webb Law Firm

(57) ABSTRACT

Provided herein is a medical device, including an instrument having a proximal end and a distal end, an introducer configured to moveably receive the instrument and having and outer housing having a proximal end, a distal end, and a sidewall therebetween defining an inner volume and an inner housing having a proximal end, a distal end, and a sidewall therebetween defining an inner volume, the inner housing slidably received within the outer housing, the distal end of the introducer configured to couple the introducer to an intravenous line. The inner housing is configured to move relative to the outer housing to move the instrument between a first position and a second position.

28 Claims, 8 Drawing Sheets

(56) References Cited

U.S. PATENT DOCUMENTS

| | | | | |
|---|---|---|---|---|
| 2014/0364766 A1* | 12/2014 | Devgon | ........... | A61B 5/150396 |
| | | | | 600/581 |
| 2017/0216564 A1* | 8/2017 | Devgon | ........... | A61B 5/150259 |
| 2018/0304021 A1 | 10/2018 | Foucher et al. | | |
| 2020/0230353 A1* | 7/2020 | Burkholz | ............... | G01N 33/49 |
| 2021/0290897 A1 | 9/2021 | Burkholz et al. | | |
| 2021/0290905 A1 | 9/2021 | Harding et al. | | |
| 2022/0218252 A1 | 7/2022 | Blanchard et al. | | |
| 2022/0218955 A1 | 7/2022 | Scherich et al. | | |
| 2022/0218956 A1 | 7/2022 | Harding et al. | | |

OTHER PUBLICATIONS

Utility U.S. Appl. No. 17/570,554, Becton, Dickinson and Company, filed Jan. 7, 2022.
Utility U.S. Appl. No. 17/709,935, Becton, Dickinson and Company, filed Mar. 31, 2022.
Utility U.S. Appl. No. 17/852,538, Becton, Dickinson and Company, filed Jun. 29, 2022.

* cited by examiner

132

116

118

110

170

180

INSTRUMENT DELIVERY DEVICE WITH NESTED HOUSING

BACKGROUND OF THE INVENTION

Field of the Invention

The present disclosure relates generally to medical devices for use with intravenous (IV) catheters and, more specifically, to medical devices with features for improving performance in terms of accessing the vasculature.

Description of Related Art

Instrument delivery devices, including those used for collecting blood, when used with indwelling IV catheters can include displaceable implements that are advanced beyond the tip of the indwelling catheter. Often, when the displaceable implement is advanced, it can encounter an obstruction, resulting in deflection of the implement. Examples of obstructions include the friction of the seal within the delivery device, torturous path within an integrated catheter, pinching of the catheter tubing as it dives into the skin, thrombus, fibrin, and valves. Further, delivery of instruments can be complicated by interchange of instruments, and the necessary length for deployment of such instruments. Accordingly, a need exists in the art for instrument delivery devices that allow for robust performance of the instrument that is being delivered.

SUMMARY OF THE INVENTION

Provided herein is a medical device, including an instrument having a proximal end and a distal end, an introducer configured to moveably receive the instrument and having an outer housing having a proximal end, a distal end, and a sidewall therebetween defining an inner volume and an inner housing having a proximal end, a distal end, and a sidewall therebetween defining an inner volume, the inner housing slidably received within the outer housing, the distal end of the introducer configured to couple the introducer to an intravenous line. The inner housing is configured to move relative to the outer housing to move the instrument between a first position, in which the instrument is disposed within the outer housing, and a second position, in which the distal end of the instrument is disposed beyond the distal end of the outer housing such that at least a first portion of the instrument is disposed within the intravenous line when the introducer is coupled to the intravenous line.

In accordance with an embodiment of the present invention, the outer housing includes a lock at the distal end thereof, the lock configured to couple the introducer to an intravenous line.

In accordance with an embodiment of the present invention, a joint is arranged at the distal end of the outer housing, optionally between the distal end of the outer housing and the lock.

In accordance with an embodiment of the present invention, the joint is a rotating joint, a ball joint, a pin joint, a cylindrical joint, a hinge joint, or a pivoting joint.

In accordance with an embodiment of the present invention, further including a flexible housing portion arranged at the distal end of the outer housing.

In accordance with an embodiment of the present invention, further including a grip arranged between the flexible housing portion and the distal end of the outer housing.

In accordance with an embodiment of the present invention, the inner housing including one or more portions including a rigid material and one or more portions including a flexible material.

In accordance with an embodiment of the present invention, the inner housing includes a flexible material and one or more portions of a rigid material overmolded over, adhered to, or co-extruded with the flexible material.

In accordance with an embodiment of the present invention, the inner housing includes a flexible material and one or more regions of a rigid material received within the flexible material.

In accordance with an embodiment of the present invention, the inner housing includes a flexible material and a rigid material, the flexible material arranged about an external surface of the rigid material.

In accordance with an embodiment of the present invention, the inner housing includes a flexible material and a rigid material, the rigid material arranged about an external surface of the flexible material.

In accordance with an embodiment of the present invention, the inner housing is rigid and the outer housing is collapsible longitudinally between a first configuration and a second configuration, wherein a length of the outer housing in the first configuration is greater than the length of the outer housing in the second configuration.

In accordance with an embodiment of the present invention, further including a septum arranged at the distal end of the outer housing.

In accordance with an embodiment of the present invention, further including a lubricant arranged at one or more locations within the inner housing.

In accordance with an embodiment of the present invention, wherein the inner housing includes a grip arranged at the proximal end thereof.

In accordance with an embodiment of the present invention, the instrument is one or more of a catheter, guidewire, obturator, wire, electrical wiring, probe, light pipe, and sensor.

In accordance with an embodiment of the present invention, the instrument is a catheter.

In accordance with an embodiment of the present invention, the inner housing includes a clamp at the proximal end thereof, configured to selectively block fluid flow through the inner housing.

In accordance with an embodiment of the present invention, the inner housing is in fluid communication with the catheter, such that fluid flowing proximally from the catheter is received within the inner housing.

In accordance with an embodiment of the present invention, the inner housing further includes a fluid conduit in fluid communication with the catheter.

In accordance with an embodiment of the present invention, the fluid conduit extends proximally beyond the proximal end of the inner housing.

In accordance with an embodiment of the present invention, a fluid conduit is coupled to the proximal end of the inner housing.

In accordance with an embodiment of the present invention, one or more supports arranged within the outer housing and configured to limit buckling of the instrument as it is advanced through the outer housing.

In accordance with an embodiment of the present invention, the inner housing is formed of a material with sufficient stiffness to limit and/or prevent buckling of the inner housing as it is advanced through the outer housing.

In accordance with an embodiment of the present invention, an inner diameter of the outer housing is configured such that buckling of the inner housing is limited and/or prevented when the inner housing is advanced through the outer housing.

In accordance with an embodiment of the present invention, one or more indicia arranged on the inner housing and corresponding to instrument length and/or instrument position relative to the intravenous catheter.

In accordance with an embodiment of the present invention, one or more indicia are visual and/or tactile indicia.

In accordance with an embodiment of the present invention, the inner housing includes a connector at the proximal end thereof.

Also provided herein is a system, including a catheter assembly including a catheter adapter having a distal end, a proximal end, a lumen extending between the distal end and the proximal end, and a side port arranged between the distal end and the proximal end, the side port in fluid communication with the lumen, a catheter secured to the distal end of the catheter adapter and extending distally from the catheter adapter, and a fluid conduit having a proximal end coupled to the side port and a distal end, the fluid conduit in fluid communication with the side port, and a medical device as described herein.

DESCRIPTION OF THE INVENTION

Figures 1A, 1B:
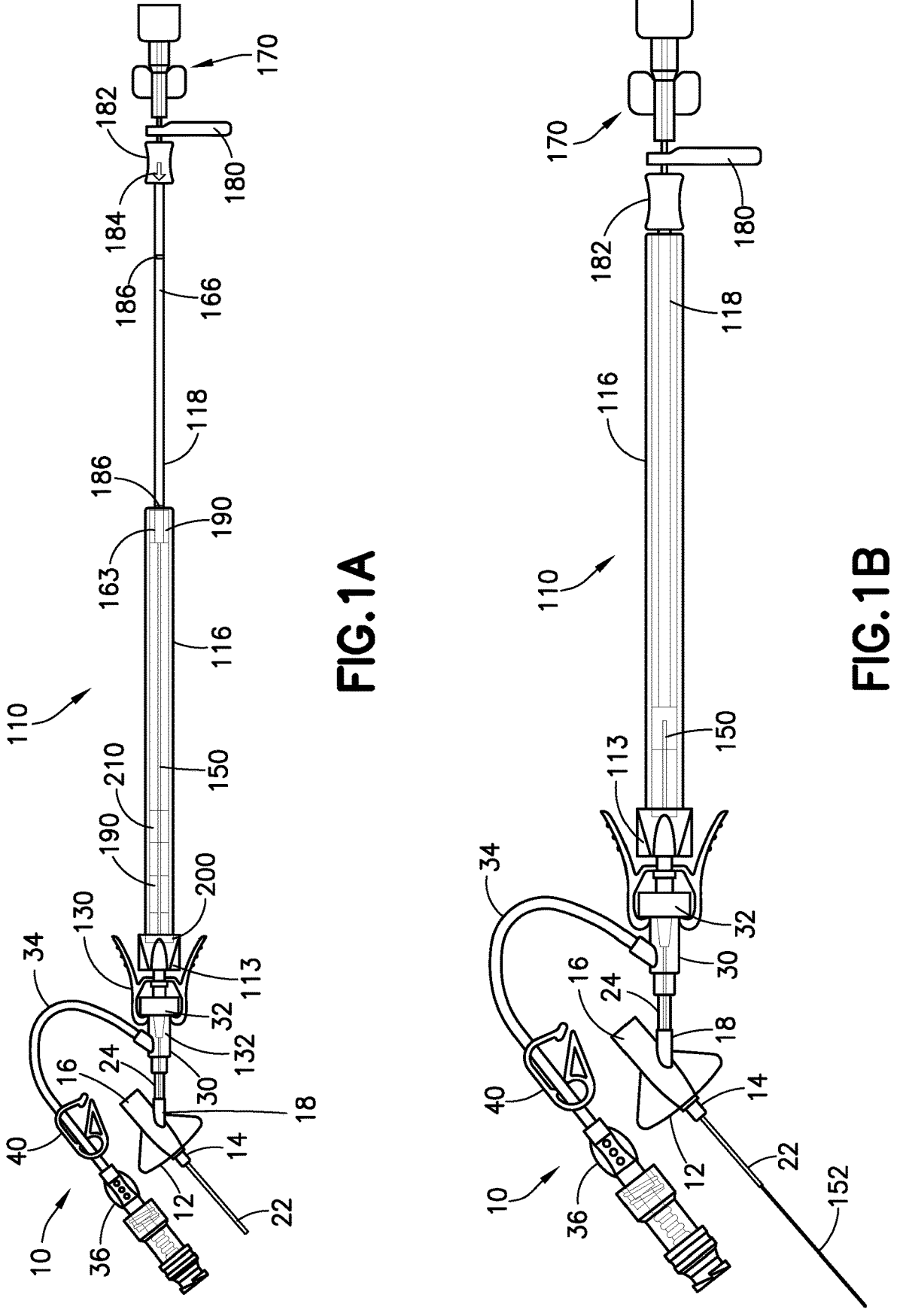
FIGS. 1A and 1B show top views of instrument delivery devices and systems according to non-limiting embodiments described herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, equivalents, variations, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

It should be understood that any numerical range recited herein is intended to include all values and sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value equal to or less than 10.

Provided herein are devices and systems for delivering instruments through indwelling catheters, such as peripheral intravenous catheters (PIVCs). While certain devices (e.g., blood draw devices) are discussed below in terms of devices that may be used with PIVCs, and exemplified in the attached drawings, those of skill will appreciate that any number of different devices for introducing an instrument, including instruments ranging from tubes, probes, sensors (e.g., pressure sensors, pH sensors, lactate sensors, glucose sensors, and the like), wiring, fiber optics, guidewires, etc., may be used within the scope of the present disclosure.

Referring now to FIGS. 1A and 1B, shown is a non-limiting embodiment of a system including a catheter assembly 10 and instrument delivery device 110. Suitable catheter assemblies for use with instrument delivery devices described herein are commercially available, for example from Becton, Dickinson and Company under the trade names Nexiva and Autoguard. Catheter assembly 10 may include a catheter adapter 12, which may include a distal end 14 and a proximal end 16. In some embodiments, the catheter adapter 12 may include one or more additional ports 18. In some embodiments, port 18 may be disposed between the distal end 14 and the proximal end 16. In some embodiments, more than one port 18 may be disposed between the distal end 14 and the proximal end 16. In some embodiments, port 18 may be disposed at proximal end 16. In some embodiments, the first catheter adapter 12 may include a first lumen 20 extending through the distal end 14 and the proximal end 16. First lumen 20 may be sealed at proximal end 16 of catheter adapter 12.

In some non-limiting embodiments or aspects, the catheter assembly 10 may include a catheter 22 extending from the distal end 14. In some embodiments, the first catheter 22 may include a peripheral intravenous catheter, arterial catheter, a midline catheter, or a peripherally-inserted central catheter. Catheter 22 may be formed of any suitable material and may be of any useful length, as known to those of skill in the art. In some non-limiting embodiments or aspects, the catheter assembly 10 may include a first fluid conduit 24 extending from the port 18. First fluid conduit 24 may be formed of any suitable material known to those of skill in the art, and may have a distal end 26 and a proximal end 28, and first fluid conduit 24 may be coupled, at distal end 26 thereof, to port 18. In some non-limiting embodiments or aspects, a connector 30 may be coupled to a proximal end 28 of first fluid conduit 24. Connector 30 may be a t-connector (e.g., one side port arranged at a 90 degree angle relative to a longitudinal axis of connector 30), a y-connector (e.g., one side port arranged between a 15 and a 165 degree angle relative to a longitudinal axis of connector 30), or any other type of connector known in the art, and may include a second lumen therethrough, having any number of branches suitable for the type of connector.

In some non-limiting embodiments or aspects, catheter assembly 10 may include an extension set (integrated into or removably coupleable to catheter adapter 12, connector 30, and/or needleless access connector 32) including a second fluid conduit, such as second fluid conduit 34. Extension sets are known to those of skill in the art and are commercially available from, for example, Becton, Dickinson and Company. In some non-limiting embodiments or aspects, second fluid conduit 34 may include a luer connection 36 at an end thereof. In some non-limiting embodiments or aspects, the extension set may include a clamp 40, to allow for occlusion of second fluid conduit 34. Clamp 40 and second fluid conduit 34 may be formed of any suitable materials known to those of skill in the art. In non-limiting embodiments, second lumen (e.g., within connector 30) has an inner diameter that is substantially equivalent to an inner diameter of first fluid conduit 24 and/or second fluid conduit 34.

Catheter assembly 10 may include a needleless access connector 32 and/or a second fluid conduit 34. Suitable needleless access connectors 32 can include any split-septum connector and/or those with direct fluid path access. Needleless access connectors 32 are known to those of skill in the art and are commercially available from, for example, Becton, Dickinson and Company under the trade names Q-SYTE, and SMARTSITE. While the non-limiting embodiments of FIGS. 1A and 1B show needleless access connectors arranged at connector 30, those of skill in the art will appreciate that suitable needleless access connectors may also be arranged at luer 36. In non-limiting embodiments, needleless access connector 32 includes a septum (not shown), such as a self-healing septum. In non-limiting embodiments, the septum is a slit-type septum. As will be described below, instrument delivery device 110 may be reversibly coupleable to the needleless access connector 32, and one or more portions of the instrument delivery device may pierce the septum and access the patient's vasculature through catheter 22.

With continuing reference to FIGS. 1A and 1B, instrument delivery device 110 includes an outer housing 116 having a proximal end and a distal end, and an inner housing 118 slidably received within outer housing 116. In non-limiting embodiments, inner housing 118 and outer housing 116 are in a telescoping relationship, such that inner housing 118 may be slidably received entirely, or almost entirely, within outer housing 116. Inner housing 118 also includes a proximal end and a distal end and, in non-limiting embodiments, inner housing may have a variable diameter along its length, for example where a distal end of inner housing 118 is of a larger diameter than other portions of inner housing 118. Instrument delivery device 110 further includes an instrument, exemplified in the drawings as catheter or fluid conduit 150 having a proximal end and a distal end 152, but, as described previously and as will be appreciated by those of skill in the art, may be any medical instrument that can be delivered through catheter assembly 10 to a patient's vasculature. Fluid conduit 150 is slidably received within outer housing 116, and may be advanced and/or retracted relative to outer housing 116 by displacement of inner housing 118 relative to outer housing 116. In non-limiting embodiments, fluid conduit 150 may be advanced from a first position, in which distal end 152 of fluid conduit 150 is within instrument delivery device 110, for example within outer housing 116 and/or lock 130, and a second position, in which a distal end 152 of fluid conduit 150 is positioned distally of lock 130 and, in embodiments in which instrument delivery device 110 is coupled to catheter assembly 10, optionally distally of catheter 22. While lock 130 is exemplified as a proboscis 132 and arms in FIGS. 1A and 1B, those of skill will appreciate that any type of suitable connection may be used to secure instrument delivery device 110 to an indwelling catheter, such as catheter assembly 10, including luer connections, clips, blunt plastic cannulae, blunt metal cannulae, hybrid luers (e.g., with a cannula) friction fits, and the like.

Instruments useful with the instrument delivery device 110 described herein may be formed of any useful material. In non-limiting embodiments, instrument is a fluid conduit, which is formed of a polymer, such a polyimide-containing material, nylon, polyurethane, and other suitable polymeric materials. In addition, inner housing 118 may be formed of any suitable material, including polyethylene, polypropylene, nylon, polyurethane, and the like. Those of skill will appreciate that various materials may be suitable, so long as they minimize potential buckling of the inner housing 118. In non-limiting embodiments, inner housing 118 is formed of a material that provides resistance to buckling, such as silicone-based materials, urethane-based materials, and the like.

As can be appreciated, FIG. 1A shows instrument delivery device in a first state, where instrument (here, fluid conduit 150) in a first position, received within outer housing 116, and inner housing 118 is in a first position, extending proximally from outer housing. In non-limiting embodiments, inner housing 118 is coupled to or otherwise interacts with fluid conduit 150, such that as inner housing 118 is advanced distally to a second position, for example by way of a user grasping grip 182 and applying a distally-directed force to inner housing 118, fluid conduit 150 is moved to a second position, where a distal end 152 of fluid conduit 150 extends beyond outer housing 116, lock 130 (if present), and/or catheter 22. Grip 182 may be arranged at a proximal end of inner housing 118, and may be arranged at or near a clamp 180 suitable for occluding fluid flow through inner housing 118 and/or fluid conduit 150, as will be described in greater detail below. Grip 182 may be formed of an ergonomic material, to provide comfort while a user grips the instrument delivery device 110, and may include features to, for example, increase grip and prevent slippage while inner housing 118 is being advanced/retracted. Clamp 180 may be a slide clamp, for example as shown in FIGS. 1A and 1B, or may be a pinch clamp.

As described above, a distal end of inner housing 118 may be of a larger diameter than other portions of inner housing 118, such that, as inner housing 118 is retracted, one or more features on outer housing 116 may interact with the enlarged portion of inner housing 118 to prevent pulling inner housing 118 completely out of outer housing 116. Enlarged distal portion of inner housing 118 may include vents for allowing air to pass therethrough, reducing force needed to advance/retract inner housing 118, and, as described below, lubricant 190 may be applied to an enlarged portion of inner housing 118 to reduce friction between inner housing 118 and outer housing 116.

Figure 3:
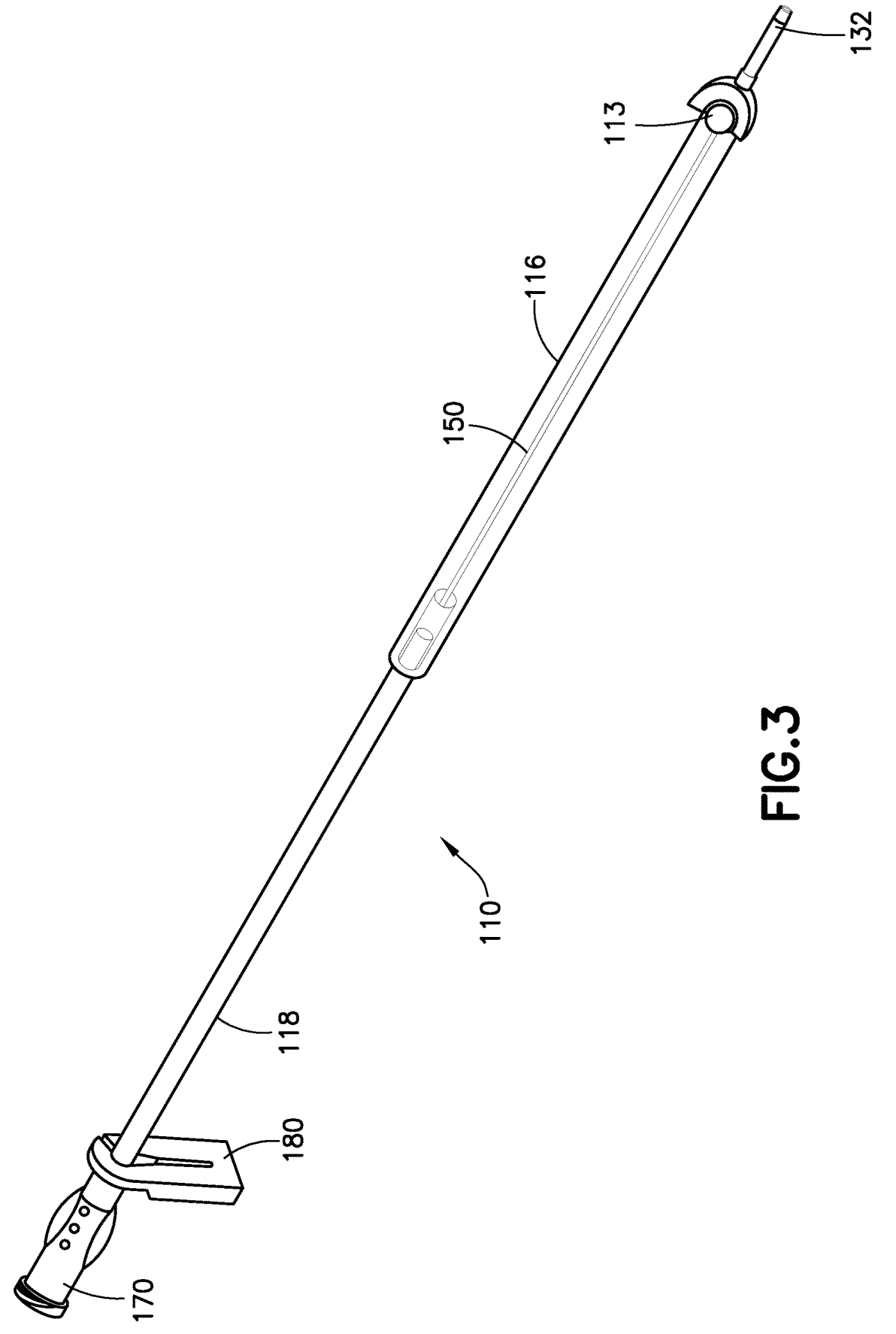
FIG. 3 shows a perspective view of an instrument delivery device according to non-limiting embodiments described herein.
Figure 4:
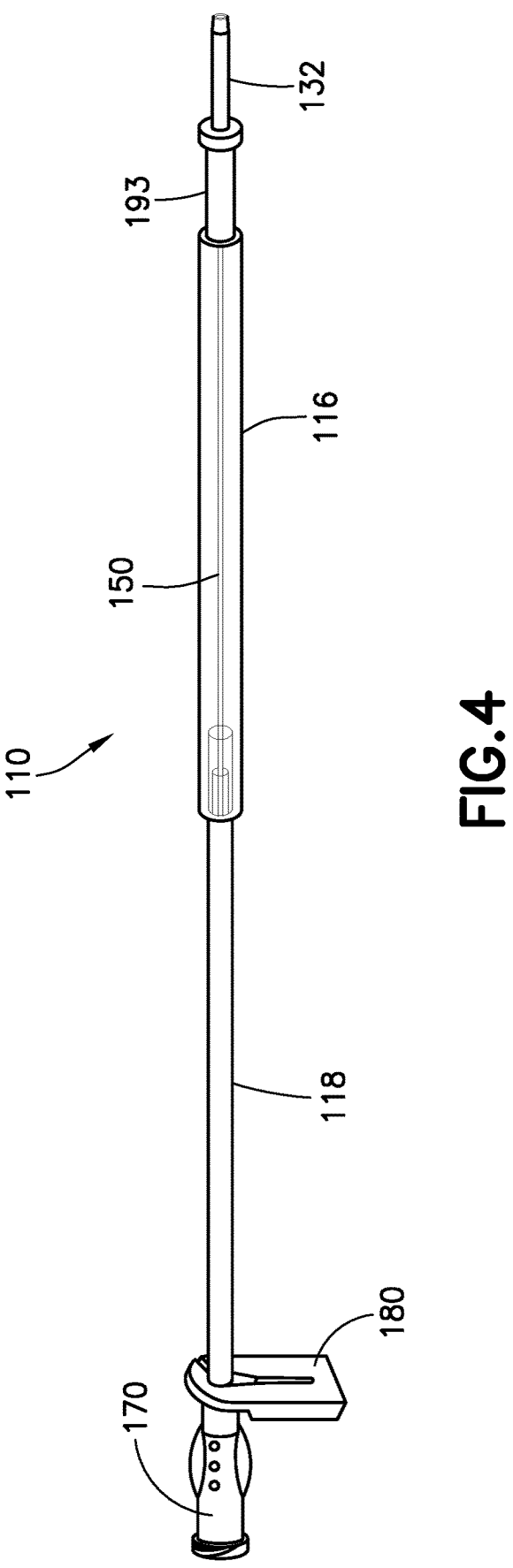
FIG. 4 shows a side view of an instrument delivery device according to non-limiting embodiments described herein.

As will be described below, and as shown in the accompanying drawings, instrument delivery device 110 may include any number of features to provide a more robust system for accessing a patient's vasculature. With continuing reference to FIGS. 1A and 1B, as well as FIGS. 2 and 3, in non-limiting embodiments a joint 113 is included at distal end of outer housing 116, for example between outer housing 116 and lock 130. Suitable joints 113 may include pivoting joints, ball joints, pin joints, cylindrical joints, hinge joints, and rotating joints. Such joints 113 may increase the usability of instrument delivery device 110, for example by allowing for greater access in terms of distance from the patient's skin, as well as securement of the indwelling catheter by avoiding excessive manipulation of the catheter assembly 10 during instrument delivery and medical procedures associated therewith. In non-limiting embodiments, proboscis 132 is formed of a flexible material to allow similar pivoting and or rotational freedom to avoid excessive manipulation of the catheter assembly 10. In non-limiting embodiments, for example as shown in FIG. 4, proboscis 132 is formed of a flexible material and is arranged at distal end of outer housing 116, and a grip 193 is arranged between proboscis 132 and distal end of outer housing 116.

Inner housing 118 may include, at a proximal end thereof, a connector 170, to allow for various medical devices to be attached to inner housing 118, for example to provide an instrument that is to be advanced into the patient's vasculature, to inject a composition into the vasculature, and/or to receive fluid withdrawn from the vasculature. Suitable connectors 170 include luer connectors, luer lock access devices, needless access connectors, and the like known to those of skill in the art.

Figure 2:
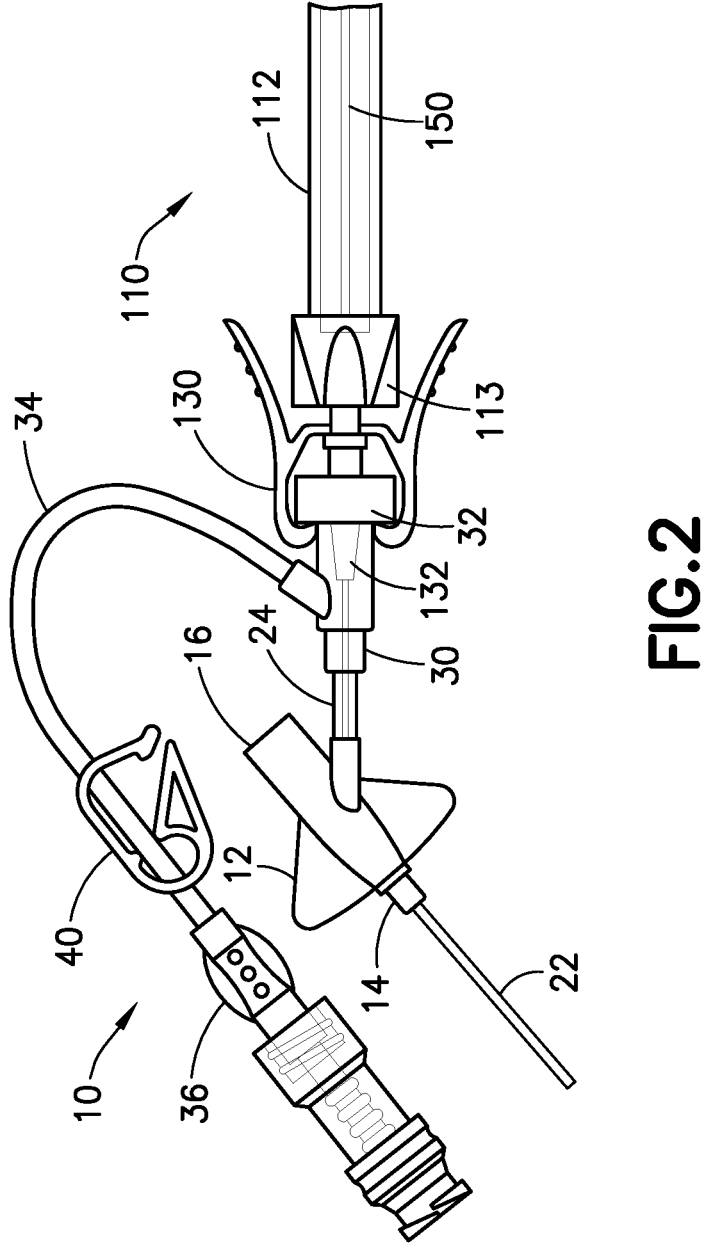
FIG. 2 shows a partial top view of an instrument delivery device and system according to non-limiting embodiments described herein.

With continuing reference to FIG. 1A, as well as FIG. 2, in non-limiting embodiments inner housing 118 may include one or more indicia 184, 186 arranged on an outer surface thereof. Suitable indicia may be visual and/or tactile, and may be provided to, for example, indicate instrument length, instrument positioning relative to indwelling catheter. In non-limiting embodiments, one or more indicia 186 may be provided on inner housing 118, and outer housing 116 may be formed of a material that is at least partially transparent, to allow for visualization of indicia 186 throughout the transition from a first position of inner housing 118 to a second position of outer housing 116. In non-limiting embodiments, a separate indicia, in the form of a tactile stop 182, may be included at one or more locations along inner housing 118, to provide a user with a tactile indication of certain thresholds. For example, a tactile stop 182 may indicate that instrument (e.g., fluid conduit 150) has nearly reached its full extension and/or may indicate that the instrument can be extended no further (for example, as shown in FIG. 1B).

With continuing reference to FIG. 1A, in non-limiting embodiments a lubricant 190 may be applied at one or more locations on or within one or more components of instrument delivery device 110. For example, a lubricant 190 may be applied to an outer surface of a distal portion (e.g., proboscis 132) of outer housing of instrument delivery device 110 that is inserted into indwelling catheter, such as catheter assembly 10, to decrease the force necessary to couple the devices together. A lubricant 190 may be applied at one or more locations within outer housing 116, for example on one or more outer surfaces of inner housing 118, one or more outer surfaces of instrument (e.g., fluid conduit 150). In non-limiting embodiments, one or more septa 200 may be arranged within outer housing 116, and a portion of instrument (e.g. fluid conduit 150) may be configured to pass therethrough. Lubricant 190 may also, or alternatively, be provided about an opening through septa 200 through which instrument (e.g., fluid conduit 150) may pass. Suitable lubricants are known to those of skill in the art, and may include silicone-based lubricants. One or more septa 200 may include air venting features to allow for ease of advancement and withdrawal of instrument (e.g., fluid conduit 150). In non-limiting embodiments, proboscis 132 is configured to provide a fluid-tight seal with catheter assembly, for example by having a diameter that is closely matched to a diameter of catheter adapter 12 and/or needless access connector 32, thereby limiting the ability of fluid to escape between an outer wall of proboscis 132 and an inner wall of catheter adapter 12 and/or needless access connector 32. Addition of a lubricant 190 on the proboscis can ease introduction of instrument delivery device 110 to catheter assembly 10, despite the closeness of the respective diameters.

With reference to FIG. 1A, in non-limiting embodiments, instrument delivery device 110 includes one or more supports 210 arranged within outer housing 116, to limit and/or prevent buckling of inner housing 118 and/or instrument (e.g., fluid conduit 150) as inner housing 118 and/or the instrument (e.g., fluid conduit 150) are advanced distally through outer housing 116. Supports 210 may include narrowed portions of outer housing 116, one or more washers arranged about inner housing 118 and/or instrument, and/or the like, for example to reduce the effective buckling length and/or buckling mode shape of inner housing 118 and/or instrument. Suitable supports are also described in U.S. Provisional Patent Application No. 63/273,226, filed Oct. 29, 2021, the contents of which are incorporated herein by reference in their entirety.

With reference to FIGS. 1A and 1B, in non-limiting embodiments, for example where instrument is a fluid conduit 150, fluid, such as blood, may be transferred into or from the patient's vasculature in which a catheter, such as catheter 22, may be indwelling. In non-limiting embodiments such as shown in FIGS. 1A and 1B, fluid conduit 150 may be joined at junction 163 to a separate fluid tube 166 that passes through inner housing 118. Separate fluid tube 166 may extend beyond a proximal end of inner housing 118, and may be coupled to connector 170, optionally through an adapter (not shown). In non-limiting embodiments, fluid conduit 150 is of a sufficient length such that it passes through inner housing 118 to couple with connector 170, optionally through an adapter. In non-limiting embodiments, inner housing 118 itself forms a fluid conduit, in fluid communication with fluid conduit 150. A separate fluid tube may be provided at proximal end of inner housing 118, and may fluidly couple inner housing 118 and connector 170, optionally through an adapter. In any of the described embodiments, an adapter may be provided to fluidly couple fluid tube 166, inner housing 118, and/or fluid conduit 150 to a connector 170, such as those described herein above.

Figure 5A:
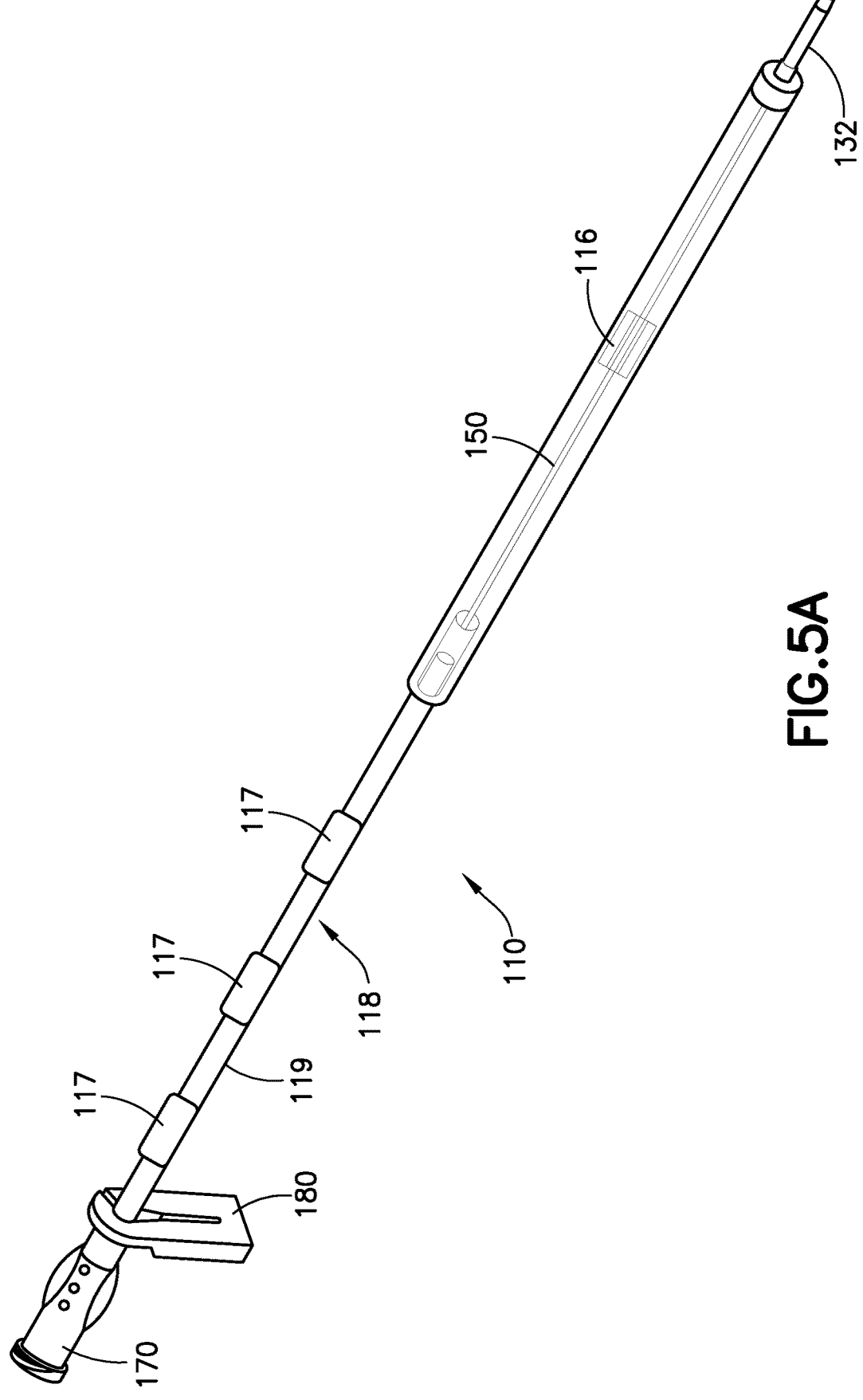
FIG. 5A shows a perspective view of an instrument delivery device according to non-limiting embodiments described herein.
Figures 1, 5B:
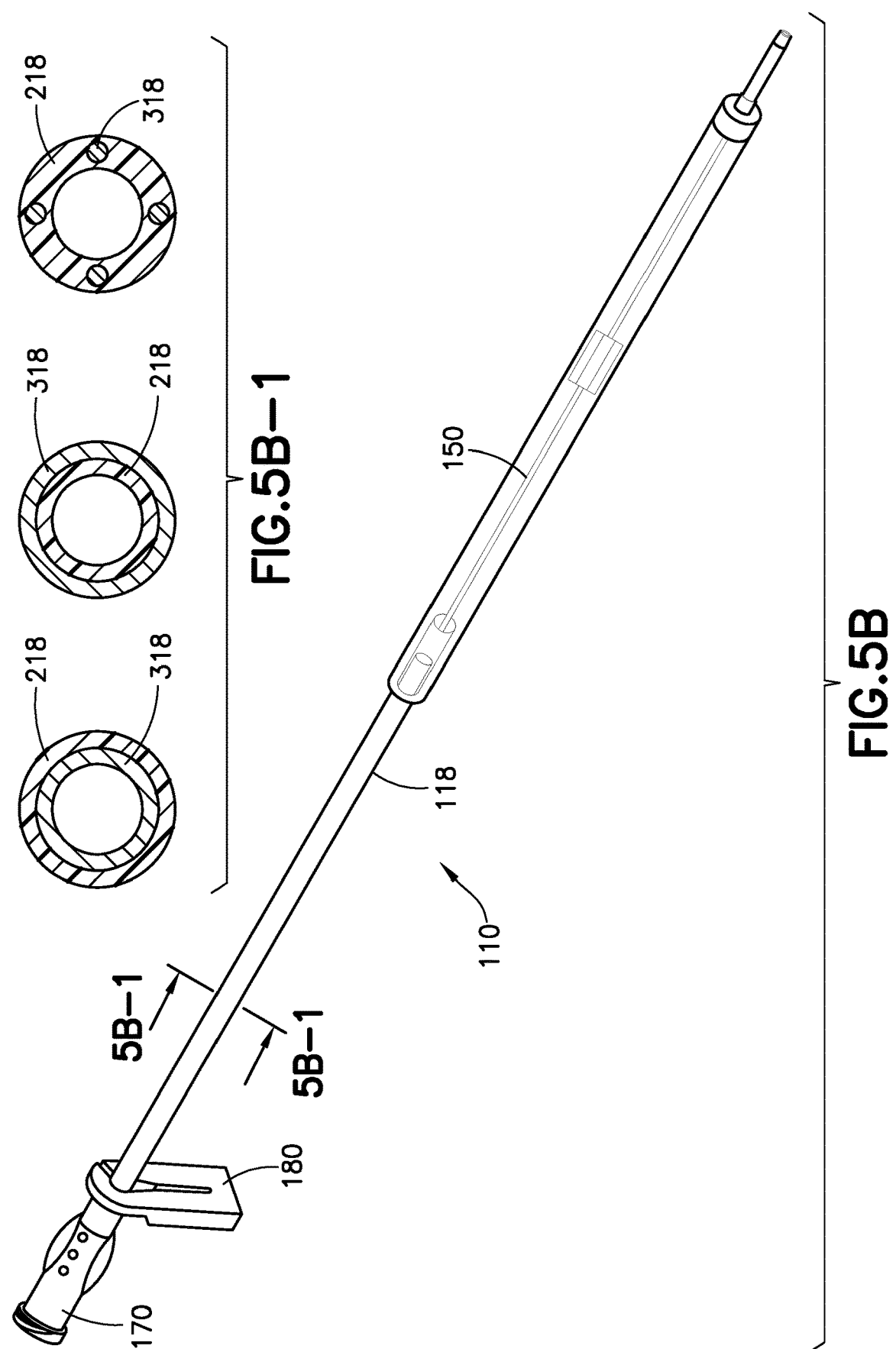
FIGS. 5B and 5B-1 show a perspective and cross-sectional views of an instrument delivery device according to non-limiting embodiments described herein.

Turning to FIGS. 5A and 5B, shown are non-limiting embodiments of various arrangements of inner housing 118 of instrument delivery device 110. Inner housing 118 may be formed of a variety of materials to provide robust instrument deployment. For example, as shown in FIG. 5A, inner housing 118 may be formed of a flexible material 119, with one or more portions of a rigid material 117 arranged therein or thereon. Suitable flexible materials are known to those of skill in the art, and include silicone-based materials, urethane-based materials, and the like. Suitable rigid materials include various plastics, such as nylon, polyetherimide, polycarbonate, or other. The rigid material 117 may be overmolded over flexible material 119 (or flexible material 119 may be overmolded over rigid material 117), may be secured to (for example, with an adhesive) flexible material 119, and/or may be co-extruded with flexible material 119. In non-limiting embodiments, one or more regions of rigid material 117 may serve as a grip for advancing inner housing 118, and, thus, elements for improved gripping may be added to one or more regions of rigid material 117. While FIG. 5A shows discrete areas of rigid material, those of skill will appreciate that rigid material may be provide at any location, with any suitable arrangement, to provide adequate flexibility and pushability of inner housing 118.

With regard to FIG. 5B, shown are a non-limiting embodiment of instrument delivery device 110, and cross-sectional views of various embodiments of inner housing 118, with flexible material 218 and rigid material 318 arranged in different configurations. As can be appreciated, flexible material 218 may be arranged about an inner and/or outer surface of rigid material 318, and rigid material 318 may similarly be arranged about an inner and/or outer surface of flexible material 218. In addition, rigid material 318 may be received within (e.g., at least partially within) flexible material 218. The arrangements of the various materials shown in the inset (FIG. 5B-1 of FIG. 5B, taken along a cross-section at 5B-1, may be substantially constant along a length of inner housing 118, may be in only discrete regions, or any combination thereof.

Figure 6A:
FIGS. 6A and 6B show a perspective views of an instrument delivery device according to non-limiting embodiments described herein.
Figure 6B:
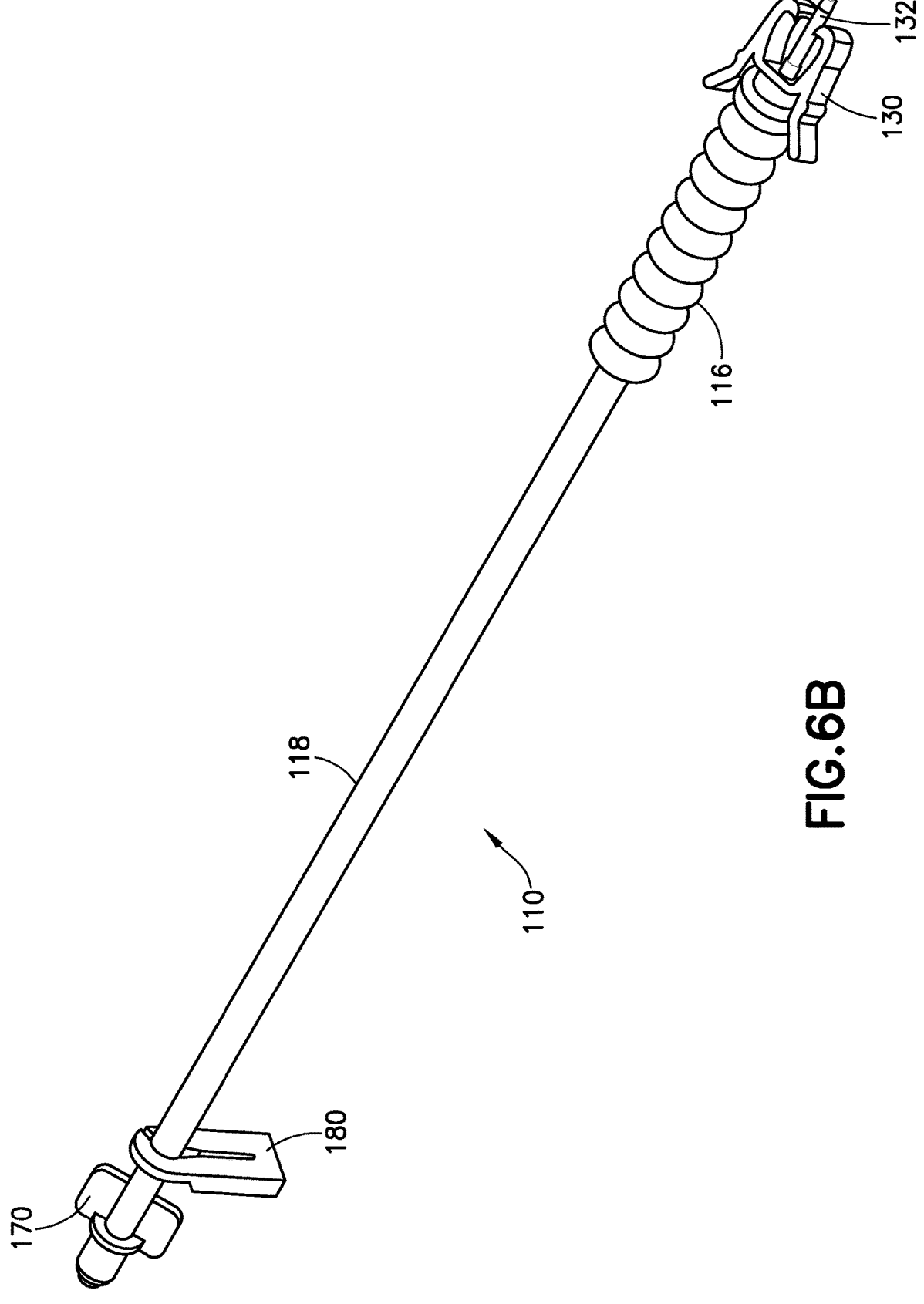

Turning to FIGS. 6A and 6B, shown are various embodiments of an instrument delivery device 110, in which outer housing 116 is collapsible. By "collapsible," it is meant that the housing (or housing portion) is capable of collapsing along a longitudinal axis, from a first, greater length to a second, lesser length. Collapsible materials and arrangements, such as an accordion arrangement, are known to those of skill in the art. With regard to FIGS. 6A and 6B, shown is an embodiment of instrument delivery device 100 in which outer housing 116 is collapsible and inner housing 118 is rigid. Outer housing 116 may be collapsible between a first, expanded configuration to a second, collapsed configuration, optionally during advancement of instrument (e.g., fluid conduit 150) by advancing inner housing 118 relative to outer housing 116. During, or following, advancement of the instrument, outer housing 116 may collapse, reducing the overall effective length of instrument delivery device 110. The non-limiting embodiment of FIG. 6A shows outer housing 116 with proboscis 132 (proboscis may be rigid or flexible, as described elsewhere herein). In the non-limiting embodiment of FIG. 6B, distal end of outer housing 116 includes a lock 130.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A medical device, comprising:
an instrument having a proximal end and a distal end;
an introducer configured to moveably receive the instrument and having:
an outer housing having a proximal end, a distal end, and a sidewall therebetween defining an inner volume; and
an inner housing having a proximal end, a distal end, and a sidewall therebetween defining an inner volume, the inner housing slidably received within the outer housing;
a distal end of the introducer configured to couple the introducer to an intravenous line; and
wherein the inner housing is configured to move relative to the outer housing and the inner housing is coupled to the instrument such that movement of the inner housing relative to the outer housing causes movement of the instrument between a first position, in which the instrument is disposed within the outer housing, and a second position, in which the distal end of the instrument is disposed beyond the distal end of the outer housing such that at least a first portion of the instrument is disposed within the intravenous line when the introducer is coupled to the intravenous line; and
wherein the inner housing comprises one or more portions comprising a rigid material and one or more portions comprising a flexible material.

2. The medical device of claim 1, wherein the outer housing comprises a lock at the distal end thereof, the lock configured to couple the introducer to the intravenous line.

3. The medical device of claim 1, wherein a joint is arranged at the distal end of the outer housing.

4. The medical device of claim 3, wherein the joint is a rotating joint, a ball joint, a pin joint, a cylindrical joint, a hinge joint, or a pivoting joint.

5. The medical device of claim 1, further comprising a flexible housing portion arranged at the distal end of the outer housing.

6. The medical device of claim 5, further comprising a grip arranged between the flexible housing portion and the distal end of the outer housing.

7. The medical device of claim 1, wherein the one or more portions comprising the rigid material are overmolded over, adhered to, or co-extruded with the one or more portions comprising the flexible material.

8. The medical device of claim 1, wherein the one or more portions comprising the rigid material are received within the one or more portions comprising the flexible material.

9. The medical device of claim 1, wherein the inner housing comprises a flexible material and a rigid material, the flexible material arranged about an external surface of the rigid material.

10. The medical device of claim 1, wherein the inner housing comprises a flexible material and a rigid material, the rigid material arranged about an external surface of the flexible material.

11. The medical device of claim 1, wherein the inner housing is rigid and the outer housing is collapsible longitudinally between a first configuration and a second configuration, wherein a length of the outer housing in the first configuration is greater than the length of the outer housing in the second configuration.

12. The medical device of claim 1, further comprising a septum arranged at the distal end of the outer housing.

13. The medical device of claim 1, further comprising lubricant arranged at one or more locations within the inner housing.

14. The medical device of claim 1, wherein the inner housing comprises a grip arranged at the proximal end thereof.

15. The medical device of claim 1, wherein the instrument is one or more of a catheter, guidewire, obturator, wire, electrical wiring, probe, light pipe, and sensor.

16. The medical device of claim 1, wherein the instrument is a catheter.

17. The medical device of claim 16, wherein the inner housing comprises a clamp at the proximal end thereof, configured to selectively block fluid flow through the inner housing.

18. The medical device of claim 17, wherein the inner housing is in fluid communication with the catheter, such that fluid flowing proximally from the catheter is received within the inner housing.

19. The medical device of claim 18, wherein the inner housing further comprises a fluid conduit in fluid communication with the catheter.

20. The medical device of claim 19, wherein the fluid conduit extends proximally beyond the proximal end of the inner housing.

21. The medical device of claim 18, further comprising a fluid conduit coupled to the proximal end of the inner housing.

22. The medical device of claim 1, further comprising one or more supports arranged within the outer housing and configured to limit buckling of the instrument as the instrument it is advanced through the outer housing.

23. The medical device of claim 1, wherein the inner housing is formed of a material with sufficient stiffness to limit and/or prevent buckling of the inner housing as the inner housing it is advanced through the outer housing.

24. The medical device of claim 1, wherein an inner diameter of the outer housing is configured such that buckling of the inner housing is limited and/or prevented when the inner housing is advanced through the outer housing.

25. The medical device of claim 1, further comprising one or more indicia arranged on the inner housing and corre-sponding to instrument length and/or instrument position relative to the intravenous catheter.

26. The medical device of claim 25, wherein the one or more indicia are visual and/or tactile indicia.

27. The medical device of claim 1, wherein the inner housing comprises a connector at the proximal end thereof.

28. A system, comprising:

a catheter assembly comprising:

a catheter adapter, comprising a distal end;

a proximal end;

a lumen extending between the distal end and the proximal end; and a side port arranged between the distal end and the proximal end, the side port in fluid communication with the lumen;

a catheter secured to the distal end of the catheter adapter and extending distally from the catheter adapter; and a fluid conduit having a proximal end coupled to the side port and a distal end, the fluid conduit in fluid communication with the side port; and the medical device of claim 1.

\* \* \* \* \*